United States Patent [19]

Van Scott et al.

[11] Patent Number: 5,258,391
[45] Date of Patent: Nov. 2, 1993

[54] PHENYL ALPHA ACYLOXYALKANOIC ACIDS, DERIVATIVES AND THEIR THERAPEUTIC USE

[76] Inventors: Eugene J. Van Scott, 3 Hidden La., Abington, Pa. 19001; Ruey J. Yu, 4 Lindenwold Ave., Ambler, Pa. 19002

[21] Appl. No.: 630,743

[22] Filed: Dec. 20, 1990

Related U.S. Application Data

[63] Continuation of Ser. No. 266,702, Nov. 3, 1988, abandoned, which is a continuation of Ser. No. 50,143, May 15, 1987, abandoned.

[51] Int. Cl.$^5$ .............. A61K 7/025; A61K 7/035; A61K 7/06; A61K 7/40; A61K 7/48; A61K 9/06; A61K 31/70; A61K 31/215
[52] U.S. Cl. ................ 514/529; 424/DIG. 5; 424/59; 424/60; 424/61; 424/62; 424/63; 424/64; 424/65; 424/69; 424/70; 514/29; 514/169; 514/533; 514/725; 514/844; 514/845; 514/846; 514/847; 514/852; 514/859; 514/860; 514/861; 514/863; 514/864; 514/873; 514/880; 514/881; 514/886; 514/887; 514/928; 514/944; 514/969
[58] Field of Search ............. 514/529, 533; 424/61

[56] References Cited

U.S. PATENT DOCUMENTS

| | | | |
|---|---|---|---|
| 3,879,537 | 4/1975 | Van Scott et al. | 514/460 |
| 3,920,835 | 11/1975 | Van Scott et al. | 514/460 |
| 4,105,783 | 8/1978 | Yu et al. | 514/459 |
| 4,216,224 | 8/1980 | Yu et al. | 514/859 X |
| 4,246,261 | 1/1981 | Van Scott et al. | 514/171 |
| 4,363,815 | 12/1982 | Yu et al. | 514/263 |
| 4,518,789 | 5/1985 | Yu et al. | 514/544 |

OTHER PUBLICATIONS

Merck Index, 1976, p. 1060; 7961.
*Current Therapy*, p. 662 (1981).
*Current Therapy*, pp. 599-603 (1984).
*The Merck Index*, 9th ed., abst 7961 (1976).

Primary Examiner—Dale R. Ore
Attorney, Agent, or Firm—Foley & Lardner

[57] ABSTRACT

Therapeutic as well as preventative measures to improve the cosmetic conditions or to alleviate the symptoms of dermatologic disorders with phenyl alpha acyloxyalkanoic acids and derivatives is disclosed. The cosmetic conditions and dermatologic disorders in humans in which the compounds may be useful include brittle or soft nails; abnormally thin skin, mucous membranes or wound; friction blisters; brittle hairs; pruritus; acne; and diseased nails, skin or mucous membranes due to natural or unnatural causes including but not limited to in flammations or infections. The phenyl alpha acyloxyalkanoic acids and derivatives include, for example, diphenyl alpha acetoxyacetic acid, phenyl alpha acetoxyacetic acid, phenyl alpha methyl alpha acetoxyacetic acid and phenyl alpha acetoxypropanoic acid. The compositions containing the active ingredients are also useful for treatment of skin, nails and hair conditions or disorders in domestic animals.

22 Claims, No Drawings

PHENYL ALPHA ACYLOXYALKANOIC ACIDS, DERIVATIVES AND THEIR THERAPEUTIC USE

This application is a continuation of application Ser. No. 07/266,702 filed Nov. 3, 1988, which is a continuation of Ser. No. 050,143, filed May 15, 1987, both now abandoned.

This invention relates generally to therapeutic as well as preventative measures to promote growing and hardening of nails, wound healing, thickening of mucous membrane, skin and its appendages by topical application of novel compositions containing phenyl alpha acyloxyalkanoic acids and derivatives thereof. As will be subsequently described in detail, we initially discovered that alpha hydroxy or keto acids and their derivatives were effective in the topical treatment of disease conditions such as dry skin, ichthyosis, eczema, palmar and plantar hyperkeratoses, dandruff, acne and warts.

We have now discovered that phenyl acyloxyalkanoic acids and derivatives on topica application promote growth and hardening of nails, thickening of lips, skin and the like.

In our prior U.S. Pat. No. 3,879,537 entitled "Treatment of Ichthyosiform Dermatoses" we described and claimed the use of certain alpha hydroxy acids, alpha keto acids and related compounds for topical treatment of fishscale like ichthyotic conditions in humans. In our U.S. Pat. No. 3,920,835 entitled "Treatment of Disturbed Keratinization" we described and claimed the use of these certain alpha hydroxy acids, alpha keto acids and their derivatives for topical treatment of dandruff, acne, and palmar and plantar hyperkeratosis.

In our prior U.S. Pat. No. 4,105,783 entitled "Treatment of Dry Skin" we described and claimed the use of alpha hydroxy acids, alpha keto acids and their derivatives for topical treatment of dry skin. In our recent U.S. Pat. No. 4,246,261 entitled "Additives Enhancing Topical Corticosteroid Action" we described and claimed that alpha hydroxy acids, alpha keto acids and their derivatives could greatly enhance the therapeutic efficacy of corticosteroids in topical treatment of psoriasis, eczema, seborrheic dermatitis and other inflammatory skin condition.

In our more recent U.S. Pat. No. 4,363,815 entitled "Alpha Hydroxy acids, Alpha Keto acids and Their Use in Treating Skin Conditions" we described and claimed that alpha hydroxy acids and alpha keto acids related to or originating from amino acids, whether or not found in proteins, were effective in topical treatment of skin disorders associated with disturbed keratinization or inflammation. These skin disorders include dry skin, ichthyosis, palmar and plantar hyperkeratosis, dandruff, Darier's disease, lichen simplex chronicus, kerotoses, acne, psoriasis, eczema, pruritus and possibly warts and herpes.

In our most recent U.S. Pat. No. 4,518,789 entitled "Phenyl Alpha-Acyloxyacetamide Derivatives and Their Therapeutic Use" we described and claimed that phenyl alpha acyloxyacetamide derivatives on topical or systemic administration were useful and effective for pruritus, atopic dermatitis, eczema, psoriasis, acne, dry skin, dandruff, malodors of integumental areas, various aches, pains and discomforts of skin, joints and other body parts in humans and domestic animals.

It has now been discovered that phenyl alpha acyloxyalkanoic acids and derivatives can be cosmetically and therapeutically useful on topical application to promote growth and hardening of nails, thickening of abnormally thin mucous membrane, skin, and for the treatment of other cosmetic and dermatologic conditions in humans and animals.

In accordance with the present invention, phenyl alpha acyloxyalkanoic acids and derivatives which are incorporated into cosmetic or therapeutic compositions for topical administrations to promote cosmetic appeal, or to alleviate the dermatologic conditions and disorders are shown by the following chemical structure.

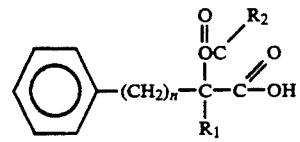

wherein
$R_1$ = H, alkyl, aralkyl or aryl group of saturated or unsaturated, straight or branched chain or cyclic form, having 1 to 25 carbon atoms,
$R_2$ = alkyl, aralkyl or aryl group of saturated or unsaturated, straight or branched chain or cyclic form, having 1 to 25 carbon atoms,
n = 0, 1, 2, 3, 4, 5.

The hydrogen atoms of phenyl group, $R_1$, $R_2$, or $(CH_2)_n$ may be substituted by a nonfunctional element or group such as F, Cl, Br, I, SH, OH, AcO or a radical such as a lower alkyl or alkoxy, saturated or unsaturated, having 1 to 9 carbon atoms.

Phenyl alpha acyloxyalkanoic acids and derivatives of the present invention may also exist as stereoisomers such as D, L, and DL forms.

The typical alkyl, aralkyl and aryl group for $R_1$ or $R_2$ includes methyl, ethyl, benzyl and phenyl. However, the preferred $R_1$ is H, methyl or phenyl group, and the preferred $R_2$ is methyl, phenyl or benzyl. The preferred n is 0 or 1. In an embodiment of this invention, $R_2$ is not methyl when n=0 and $R_1$=H. Since the compound is an organic carboxylic acid in nature, it may form a salt, a lactone or a complex with an inorganic or organic base such as ammonium hydroxide, sodium or potassium hydroxide, or triethanolamine.

Representative phenyl alpha acyloxyalkanoic acids and derivatives which are useful for topical application to promote growing and hardening of nails, wound healing and to enhance thickening of mucous membrane, skin and its appendages, and to treat other cosmetic and dermatologic conditions and disorders are listed as follows:

1. Phenyl alpha acetoxyacetic acid
   $R_1$=H, $R_2$=$CH_3$, n=0
2. Phenyl alpha acetoxypropanoic acid
   $R_1$=H, $R_2$=$CH_3$, n=1
3. Phenyl alpha methyl alpha acetoxyacetic acid
   $R_1$=$CH_3$, $R_2$=$CH_3$, n=0
4. Phenyl alpha methyl alpha acetoxypropanoic acid
   $R_1$=$CH_3$, $R_2$=$CH_3$, n=1
5. Diphenyl alpha acetoxyacetic acid
   $R_1$=$C_6H_5$, $R_2$=$CH_3$, n=0
6. Dibenzyl alpha acetoxyacetic acid
   $R_1$=$C_6H_5CH_2$, $R_2$=$CH_3$, n=1
7. Phenyl alpha benzyl alpha acetoxyacetic acid
   $R_1$=$C_6H_5CH_2$, $R_2$=$CH_3$, n=0
8. Phenyl alpha benzoyloxyacetic acid
   $R_1$=H, $R_2$=$C_6H_5$, n=0
9. Phenyl alpha methyl alpha benzoyloxyacetic acid $R_1=CH_3, R_2=C_6H_5, n=0$
10. Diphenyl alpha benzoyloxyacetic acid
   $R_1=C_6H_5, R_2=C_6H_5, n=0$
11. Phenyl alpha phenylacetoxyacetic acid
   $R_1=H, R_2=C_6H_5CH_2, n=0$
12. Phenyl alpha methyl alpha phenylacetoxyacetic acid
   $R_1=CH_3, R_2=C_6H_5CH_2, n=0$
13. Diphenyl alpha phenylacetoxyacetic acid
   $R_1=C_6H_5, R_2=C_6H_5CH_2, n=0$ Phenyl alpha acyloxyalkanoic acid derivatives which may be useful for topical application to promote growth and hardening of nails, thickening of abnormally thin mucous membrane and skin, and other cosmetic and dermatologic conditions are listed below:
4-Hydroxyphenyl alpha acetoxyacetic acid
4-Acetoxyphenyl alpha acetoxyacetic acid
4-Chlorophenyl alpha acetoxyacetic acid
3-Hydroxy-4-methoxyphenyl alpha acetoxyacetic acid
4-Hydroxy-3-methoxyphenyl alpha acetoxyacetic acid
3-(2-Hydroxyphenyl) alpha acetoxypropanoic acid
3-(4-Hydroxyphenyl) alpha acetoxypropanoic acid
2-Phenyl beta acetoxypropanoic acid Phenyl alpha acyloxyalkanoic acids and derivatives of the instant invention may also be utilized in combination with or as additives to enhance cosmetic or therapeutic effects of other cosmetics or dermatologic drugs. The dermatologic drugs may include but are not limited to corticosteroids of either synthetic or nonsynthetic origin, and antimicrobial agents. For example, such corticosteroids include hydrocortisone, hydrocortisone-21-acetate, hydrocortisone-17-valerate, hydrocortisone-17-butyrate, triamcinolone acetonide, betamethasone dipropionate and clobetasol propionate. The antimicrobial agents include antiyeast, anti-fungal, antibacterial and antiviral drugs. For example, such antimicrobial and other dermatologic agents include clotrimazole, miconazole, nystatin, neomycin, gramicidin, haloprogin, minoxidil, erythromycin, tetracycline, griseofulvin, salicylic acid, selenium sulfide, zinc pyrithione, crotamiton, lindane, amphotericin, sodium thiosulfate, phenol, menthol, anthralin, diphenhydramine, other antihistamine drugs and the like.

It has already been established through tests in humans that phenyl alpha acyloxyalkanoic acids and derivatives of this invention are cosmetically and therapeutically effective for topical application to help grow and harden nails. The compounds of this invention have also been proven effective to thicken and normalize lips to counteract the side effects caused by oral administration of retinoids such as isotretinoin (Accutane). It has also been shown through tests in humans that the compounds of the instant invention can help thicken the skin, including palms and soles and consequently could prevent the formation of friction blisters.

It has also been established through tests in patients having ileostomy or colostomy that phenyl alpha acyloxyalkanoic acids and derivatives of this invention are therapeutically effective in topical applications to help in healing of ulcerated peri-stomal skin and to enhance keratinization for the development of normal skin.

Accordingly, it is an object of this invention to provide medicinal as well as cosmetic compositions containing at least one of the phenyl alpha acyloxyalkanoic acids or a derivative thereof which, when topically administered, will help grow and harden defective nails, and will normalize skin and lips.

It is another object of this invention to provide methods for treating cosmetic and dermatologic conditions with topical preparations containing phenyl alpha acyloxyalkanoic acids and derivatives thereof.

The following are examples of typical formulations of compositions of this invention which may use any of the phenyl alpha acyloxyalkanoic acids or derivatives identified herein. These examples are illustrative and not intended to be limitative.

Preparation of the Cosmetic and Therapeutic Compositions

Phenyl alpha acyloxyalkanoic acids and derivatives may be formulated for topical application in solution, lotion, gel, shampoo, spray, stick, powder, cream, or ointment containing from 0.01 to 50 percent and preferably from 0.1 to 10 percent by weight of said active ingredient(s).

To prepare a typical solution for nails and scalps, phenyl alpha acyloxyalkanoic acids and derivatives are dissolved in a solution prepared from acetone, ethanol and water in a volume ration of 20:50:30 respectively. Alternatively, a cosmetic or therapeutic solution containing phenyl alpha acyloxyalkanoic acids and derivatives may also be prepared from a mixture of ethanol, water and propylene glycol in a volume ration of 50:40:10 respectively. A typical cosmetic or therapeutic solution may contain 2 to 5% of phenyl alpha acyloxyalkanoic acids and derivatives.

Phenyl alpha acyloxyalkanoic acid in a lotion or cream composition may be formulated as follows. Phenyl alpha acyloxyalkanoic acid one part is dissolved in two parts of ethanol and the solution thus obtained is mixed with an oil-in-water lotion or cream base such as hydrophilic ointment U.S.P. The preferred concentration of phenyl alpha acyloxyalkanoic acid in the lotion or cream ranges from 1 to 5% by weight of the total composition.

Phenyl alpha acyloxyalkanoic acid in non-aqueous ointment may be formulated as follows. Phenyl alpha acyloxyalkanoic acid one part is dissolved in two parts of ethanol and the solution thus obtained is mixed with an ointment prepared from two parts of petrolatum and one part of mineral oil. The preferred concentration of phenyl alpha acyloxyalkanoic acid in the ointment for lips or wound healing ranges from 1 to 5% by weight of the total composition.

A typical gel composition of this invention utilizes at least one of the phenyl alpha acyloxyalkanoic acids and derivatives dissolved in a mixture of ethanol, water and propylene glycol in a volume ratio of 40:40:20 respectively. A gelling agent such as hydroxyethylcellulose, hydroxypropylcellulose or hydroxypropylmethylcellulose is then added to the mixture with agitation. The preferred concentration of the gelling agent may range from 0.1 to 3 percent by weight of the total composition. The preferred concentration of the phenyl alpha acyloxyalkanoic acid in the gel composition ranges from 1 to 8 percent by weight of the total composition.

The following are illustrative examples of syntheses, formulations and compositions according to this invention. Although the examples utilize only selected formulations useful according to this invention, it should be understood that the following examples are illustrative and not limited Therefore, any of the aforementioned phenyl alpha acyloxyalkanoic acids or derivatives may be substituted according to the teachings of this invention in the following examples:

EXAMPLE 1

The following methods may be applied to synthesis of all phenyl alpha acyloxyalkanoic acids.

Diphenyl glycolic acid (benzilic acid) 80 g is dissolved in 300 ml of acetic anhydride and concentrated sulfuric acid 0.5 ml is added. The mixture is heated to 90 C. for 5 hours and is evaporated under vacuum to remove acetic acid and the excess acetic anhydride. The residue is then washed with water. The crude product thus obtained is dissolved in 250 ml of hot ethanol and the solution is mixed with 1 liter of cold water. Crystals thus obtained are washed with water and dried in 40C. in vacuum. Diphenyl alpha acetoxyacetic acid 96 g thus synthesized is identified by infrared spectroscopy, high performance liquid chromatography and thin-layer chromatography with a mobility of 0.68 on a solvent system of benzene:methanol 1.1.

Alternatively, diphenyl alpha acetoxyacetic acid may be synthesized as follows. Benzilic acid 69 g is dissolved in 320 ml of pyridine, and acetyl chloride 53 ml is slowly added from a separatory funnel while the mixture is cooled externally with an ice-water bath. After 16 hours at room temperature the mixture is mixed with 2 liters of water. The sticky product thus separated out is extracted with 300 ml of chloroform. The chloroform solution is washed with dilute HCl, dried over anhydrous sodium sulfate and is evaporated in vacuum to give 70 g of diphenyl alpha acetoxyacetic acid. The product thus synthesized is identical to the compound prepared by the above first method as shown by infrared spectroscopy, high performance liquid chromatography and thin-layer chromatography.

EXAMPLE 2

A typical therapeutic solution containing phenyl alpha acyloxyacetic acid derivative for nails and for scalps is formulated as follows.

Diphenyl alpha acetoxyacetic acid 4 g is dissolved in 96 ml of a solution prepared from acetone, ethanol and water 2:5:3. The solution thus prepared contains 4% diphenyl alpha acetoxyacetic acid as an active ingredient.

EXAMPLE 3

A typical therapeutic ointment containing a phenyl alpha acyloxyakanoic acid for lips or wound healing is formulated as follows.

Phenyl alpha acetoxyacetic acid 3 g is dissolved in 4 ml of ethanol, and the solution thus obtained is mixed with 66 g of petrolatum and 27 g of mineral oil. The ointment thus prepared contains 3% phenyl alpha acetoxyacetic acid as an active ingredient.

EXAMPLE 4

A typical therapeutic cream containing a phenyl alpha acyloxyalkanoic acid for nails of psoriasis is formulated as follows.

Phenyl alpha acetoxyacetic acid 2 g is dissolved in 10 ml of propylene glycol, and the solution thus obtained is mixed with 88 g of commonly available oil in water emulsion such as hydrophilic ointment U.S.P. The cream thus prepared contains 2% phenyl alpha acetoxyacetic acid as an active ingredient.

EXAMPLE 5

Synthesis of DL-phenyl alpha acetoxypropanoic acid

DL-$\beta$-phenyllactic acid 10 g is suspended in 50 ml of acetic anhydride and concentrated sulfuric acid 0.1 ml is added with stirring The mixture becomes a clear solution, with a slight exothermic reaction. The acetylation is completed by heating the mixture for one hour at 80-85 C. The mixture is then mixed with 800 ml of iee-water. An oily layer separated at the bottom of the mixture is extracted with 80 ml of chloroform. The chloroform layer is separated, washed with water, and dried over anhydrous sodium sulfate. After evaporation a syrupy product 12 g is obtained. DL-phenyl alpha acetoxypropanoic acid thus synthesized is identified by infrared spec troscopy, high performance liquid chromatography and thin-layer chromatography with a mobility of 0.45 on a solvent system of benzene:methanol 1:1.

EXAMPLE 6

A therapeutic powder composition containing a phenyl alpha acyloxyalkanoic acid for ileostomy or colostomy patients having ulcerated or extremely thin peri-stomal skin may be formulated as follows.

Phenyl alpha acetoxyacetic acid 2 g in a fine powder form is mixed with 98 g of commercially available powder preparation for ileostomy or colostomy. The mixing is continued until a uniform composition is obtained. The powder composition thus formulated contains 2% phenyl alpha acetoxyacetic acid as an active ingredient.

EXAMPLE 7

A therapeutic paste composition containing a phenyl alpha acyloxyalkanoic acid for ileostomy or colostomy patients having ulcerated or extremely thin peri-stomal skin may be formulated as follows.

Phenyl alpha acetoxyacetic acid 2 g is dissolved in 8 ml of propylene glycol, and the solution thus prepared is mixed with 90 g of commercially available paste preparation for ileostomy or colostomy. The mixing is continued until a uniform composition is obtained The paste composition thus formulated contains 2% phenyl alpha acetoxyacetic acid as an active ingredient.

Test Results

1. Toxicity: Five mice were given each phenyl alpha acyloxyalkanoic acid or derivative compounds of this invention as single subcutaneous injections at various doses. It was found that all the phenyl alpha acyloxyalkanoic acids and derivatives tested at doses up to 1 g/kg of body weight were nontoxic, i.e. all mice were alive and healthy at the end of 4 weeks after the administration of the test substance.

2. Screening for Hyperkeratogenic Effect: Both hairless and rhino mice might be used in these studies. Phenyl alpha acyloxyalkanoic acid or derivative compounds of this invention prepared as a 10% solution or cream form was topically applied once daily on the midbacks of at least 3 mice each, 5 days weekly for 2 weeks. At the end of test period, biopsy samples of treated and untreated skin were taken and stained histologically and were examined microscopically.

In hairless mice treated with phenyl alpha acyloxyalkanoic acid or derivatives of this invention the skin became thickened with formation of many comedones, and the stratum corneum showed compact and increased thickness. In rhino mice treated with phenyl alpha acyloxyalkanoic acid or derivative the skin became extremely thickened and saturated with increased numbers of comedone impactions in the follicular utriculi.

The results showed that in both cases of hairless and rhino mice phenyl alpha acyloxyalkanoic acid or derivative on topical administration to the skin had caused substantially increased keratinization and had made the skin hard and tough.

3. Brittle Finger Nails: A total of 14 women having brittle nails participated in this study. The brittle nails are Characterized by the following: (a) transverse longitudinal splitting, (b) thinness and (c) brittleness. Past histories of the patients revealed that the duration of such nail problems ranged from one to 20 years.

Therapeutic compositions containing phenyl alpha acyloxyalkanoic acids prepared in solution form as described in Examples were provided to the participating subjects. The patients were instructed to apply topically the medication once daily to base of nails at the nail fold. Topical applications of the compositions were continued for 6 to 9 months.

Within four to six months, substantial improvement of the brittle nails was clinically detectable. All the nails treated with compositions containing phenyl alpha acyloxyalkanoic acids became thicker, rigid, and less friable. Transverse splitting of nails no longer occurred and the finger nails were normal.

4. Psoriasis of Finger Nails: Psoriasis of finger nails usually occur in patients having skin lesions of psoriasis. A total of 27 patients; 16 men and 11 women having psoriasis of finger nails participated in this study. The involved nails were characterized by one or more of the following: (a) separation of the nail plate from the nailbed distally; (b) friability, and structurally softer than normal, and distal portions often non-existent; (c) structural distortions, for example, irregular surfaces, pits and loss of nails near the nail groove. The duration of nail problems ranged from 3 months to 12 years.

Therapeutic compositions containing phenyl alpha acyloxyalkanoic acids prepared in solution or cream form as described in examples were provided to the participating patients The patients were instructed to apply topically the medication twice daily to all areas of the affected nails. Topical applications of the compositions were continued for 3-9 months.

Distinct clinical improvement of the nails was detected within one to two months from beginning topical application of medications containing phenyl alpha acyloxyalkanoic acids. Normalization of the nail usually occurred at a rate commensurate with the growth rate of normal nails, which in most adults is 1 mm per week. For example, if the distal 4 mm of nail were affected a normal nail would be present at the end of approximately one month. If the entire nail was affected, either entirely distorted or even absent, a normal nail would require 6 months or longer to grow. On continued use of the compositions containing phenyl alpha acyloxyalkanoic acids the finger nails of the majority of psoriatic patients grew normally and were maintained free of disease clinically.

5. Cheilitis: A total of 19 patients, 9 men and 10 women having peeling of lips secondary to therapy with oral 13-cis retinoic acid (isotretinoin) participated in this study. Cheilitis is characterized by severe peeling, orally, which in these patients varied from 10 to 40 mg daily. This type of cheilitis usually occurred within one week after oral iso-tretinoin was started.

Therapeutic compositions containing phenyl alpha acyloxyalkanoic acids prepared in cream or ointment form as described in Examples were provided to the patients having cheilitis. The patients were instructed to apply topically the medication two to four times daily to the affected lips.

Within 2 to 4 days, signs of cheilitis disappeared completely and the lips appeared normal clinically. On continued use of the compositions containing phenyl alpha acyloxyalkanoic acids, the lips of patients taking oral iso-tretinoin were maintained in a clinically normal state.

6. Ileostomy and Colostomy: Three patients with ileostomy and one patient with colostomy participated in these studies. Prior to their participation all four patients had ulceration of peri-stomal skin, of years duration, and thin epidermis easily denuded by slight trauma.

Therapeutic compositions containing phenyl alpha acyloxyalkanoic acids prepared in both powder and paste forms as described in the Examples were provided to the patients having ileostomy or colostomy. The patients were instructed to apply first the paste preparation then the powder preparation on the affected areas of skin prior to attachment of ostomy ring and bag. Such applications were continued for several weeks. Complete healing of the ulcerated skin occurred within 3 weeks of time. The denuded areas of skin usually became covered with epidermis which over the ensuing 2 weeks of time became thicker and developed an intact stratum corneum.

The invention may be embodied in other specific forms without departing from the spirit or essential characteristics thereof. The present embodiments are therefore to be considered in all respects as illustrative and not restrictive, the scope of the invention being indicated by the appended claims and all changes which come within the meaning and equivalency of the claims are therefore intended to be embraced therein.

We claim:

1. A composition suitable for topical administration to nails, skin, lips and other mucous membranes, said composition comprising at least one compound selected from the group consisting of 2-phenyl beta acetoxypropanoic acid, and phenyl alpha acyloxyalkanoic acids having the formula:

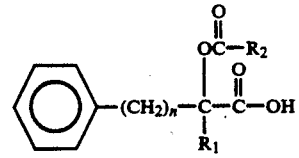

wherein said compound is present as free acid, lactone or salt form, and as an optically active or inactive isomer selected from the group consisting of D, L, and DL form, and wherein $R_1$ represents H, alkyl, aralkyl or aryl group of saturated or unsaturated, straight or branched chain, having 1 to 25 carbon atoms, or a cyclic form, $R_2$ represents methyl, ethyl, phenyl or benzyl, n is 0, 1, 2, 3, 4 or 5, and the hydrogen atoms of the phenyl, $R_1$, $R_2$, $(CH_2)_n$ may be substituted by a halogen, hydroxy, acetoxy, sulfur, or a lower alkyl or alkoxy, saturated or unsaturated having 1 to 9 carbon atoms, wherein said compound is other than phenyl alpha acetoxyacetic acid, and wherein said at lest one compound is present in said composition in an amount sufficient to enhance keratinization of nails, skin, lips and other mucous membranes.

2. The composition of claim 1 wherein the phenyl alpha acyloxyalkanoic acid or derivative is a member selected from the group consisting of
1. Phenyl alpha acetoxypropanoic acid;
2. Phenyl alpha methyl alpha acetoxyacetic acid;
3. Phenyl alpha methyl alpha acetoxypropanoic acid;
4. Diphenyl alpha acetoxyacetic acid;
5. Dibenzyl alpha acetoxyacetic acid;
6. Phenyl alpha benzyl alpha acetoxyacetic acid;
7. Phenyl alpha benzoyloxyacetic acid;
8. Phenyl alpha methyl alpha benzoyloxyacetic acid;
9. Diphenyl alpha benzoyloxyacetic acid;
10. Phenyl alpha phenylacetoxyacetic acid;
11. Phenyl alpha methyl alpha phenylacetoxyacetic acid;
12. Diphenyl alpha phenylacetoxyacetic acid;
13. 4-hydroxyphenyl alpha acetoxyacetic acid;
14. 4-acetoxyphenyl alpha acetoxyacetic acid;
15. 4-chlorophenyl alpha acetoxyacetic acid;
16. 3-hydroxy-4-methoxyphenyl alpha acetoxyacetic acid;
17. 4-hydroxy-3-methoxyphenyl alpha acetoxyacetic acid;
18. 3-(2-hydroxyphenyl) alpha acetoxypropanoic acid;
19. 3-(4-hydroxyphenyl) alpha acetoxypropanoic acid; and
20. 2-phenyl beta acetoxypropanoic acid.

3. The composition of claim 1 further comprising a carrier suitable for topical administration.

4. The composition of claim 1, wherein said nails are brittle nails or psoriatic nails.

5. A composition according to claim 1, wherein said at least one compound is 2-phenyl beta acetoxypropanoic acid.

6. A composition according to claim 1, wherein said at least one compound is phenyl alpha acetoxypropanoic acid.

7. A composition according to claim 1, wherein said at least one compound is diphenyl alpha acetoxyacetic acid.

8. A composition according to claim 1, wherein said skin is peristomal skin.

9. A composition according to claim 1, wherein said at least one compound is present in said composition in an amount sufficient to enhance keratinization of brittle nails.

10. A composition according to claim 1, wherein said at least one compound is present in said composition in an amount sufficient to enhance keratinization of psoriatic nails.

11. A method for enhancing keratinization of nails, skin, lips and other mucous membranes comprising topically administering a composition comprising at least one compound selected from the group consisting of 2-phenyl beta acetoxypropanoic acid, and phenyl alpha acyloxyalkanoic acids having the formula:

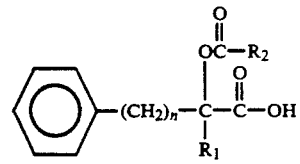

wherein said compound is present as free acid, lactone or salt form, and as an optically active or inactive isomer selected from the group consisting of D, L, and DL form, and wherein $R_1$ represents H, alkyl, aralkyl or aryl group of saturated or unsaturated, straight or branched chain, having 1 to 25 carbon atoms, or a cyclic form, $R_2$ represents methyl, ethyl, phenyl or benzyl, n is 0, 1, 2, 3, 4 or 5, and the hydrogen atoms of the phenyl, $R_1$, $R_2$, $(CH_2)_n$ may be substituted by a halogen, hydroxy, acetoxy, sulfur, or a lower alkyl or alkoxy, saturated or unsaturated having 1 to 9 carbon atoms, wherein said at least one compound is present in said composition in an amount sufficient to enhance keratinization of nails, skin, lips and other mucous membranes.

12. The method of claim 11, wherein the composition further comprises a carrier suitable for topical administration.

13. The method of claim 11 wherein the phenyl alpha acyloxyalkanoic acid or derivative is a member selected from the group consisting of
1. Phenyl alpha acetoxyacetic acid;
2. Phenyl alpha acetoxypropanoic acid;
3. Phenyl alpha methyl alpha acetoxyacetic acid;
4. Phenyl alpha methyl alpha acetoxypropanoic acid;
5. Diphenyl alpha acetoxyacetic acid;
6. Dibenzyl alpha acetoxyacetic acid;
7. Phenyl alpha benzyl alpha acetoxyacetic acid;
8. Phenyl alpha benzoyloxyacetic acid;
9. Phenyl alpha methyl alpha benzoyloxyacetic acid;
10. Diphenyl alpha benzoyloxyacetic acid;
11. Phenyl alpha phenylacetoxyacetic acid;
12. Phenyl alpha methyl alpha phenylacetoxyacetic acid;
13. Diphenyl alpha phenylacetoxyacetic acid;
14. 4-hydroxyphenyl alpha acetoxyacetic acid;
15. 4-acetoxyphenyl alpha acetoxyacetic acid;
16. 4-chlorophenyl alpha acetoxyacetic acid;
17. 3-hydroxy-4-methoxyphenyl alpha acetoxyacetic acid;
18. 4-hydroxy-3-methoxyphenyl alpha acetoxyacetic acid;
19. 3-(2-hydroxyphenyl) alpha acetoxypropanoic acid;
20. 3-(4-hydroxyphenyl) alpha acetoxypropanoic acid; and
21. 2-phenyl beta acetoxypropanoic acid.

14. The method of claim 11, wherein said nails are brittle nails or psoriatic nails.

15. A method according to claim 11, wherein said at least one compound is phenyl alpha acetoxyacetic acid.

16. A method according to claim 11, wherein said at least one compound is phenyl alpha acetoxypropanoic acid.

17. A method according to claim 11, wherein said at least one compound is diphenyl alpha acetoxyacetic acid.

18. A method according to claim 11, wherein said skin is peristomal skin.

19. A method according to claim 11, wherein said at least one compound is present in said composition in an amount sufficient to enhance keratinization of brittle nails.

20. A method according to claim 11, wherein said at least one compound is present in said composition in an amount sufficient to enhance keratinization of psoriatic nails.

21. A method according to claim 15, wherein said composition is topically administered to lips.

22. A method according to claim 15, wherein said composition is topically administered to nails.

* * * * *